(12) United States Patent
Wachendorff-Neumann et al.

(10) Patent No.: US 6,444,693 B1
(45) Date of Patent: Sep. 3, 2002

(54) FUNGICIDAL ACTIVE SUBSTANCE COMBINATIONS

(75) Inventors: Ulrike Wachendorff-Neumann, Neuwied; Klaus Stenzel, Düsseldorf; Thomas Seitz, Langenfeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/890,404

(22) PCT Filed: Jan. 24, 2000

(86) PCT No.: PCT/EP00/00505

§ 371 (c)(1),
(2), (4) Date: Jul. 30, 2001

(87) PCT Pub. No.: WO00/45638

PCT Pub. Date: Aug. 10, 2000

(30) Foreign Application Priority Data

Feb. 2, 1999 (DE) .......................................... 199 04 081

(51) Int. Cl.$^7$ .......................... A01N 43/50; A01N 47/10
(52) U.S. Cl. ........................ 514/386; 514/478; 514/479
(58) Field of Search ................................ 514/386, 478, 514/479

(56) References Cited

U.S. PATENT DOCUMENTS

| 5,650,423 A | 7/1997 | Dehne et al. ................ 514/376 |
| 6,245,772 B1 | 6/2001 | Dehne et al ................ 514/269 |

*Primary Examiner*—Allen J. Robinson
(74) *Attorney, Agent, or Firm*—Joseph C. Gil; Raymond J. Harmuth

(57) ABSTRACT

The invention relates to novel active substance combinations of valinamide derivatives of formula (I), wherein $R^1$ and $R^2$ have the meaning cited in the description, and fenamidone. The invention also relates to the use of novel active substance combinations to combat phytopathogenic fungi.

6 Claims, No Drawings

FUNGICIDAL ACTIVE SUBSTANCE COMBINATIONS

This application is a 371 of PCT/EP00/00505, filed Jan. 24, 2000.

The present application relates to novel active compound combinations comprising on the one hand valinamide derivatives and on the other hand fenamidone and which are highly suitable for controlling phytopathogenic fungi.

It is already known that valinamide derivatives have fungicidal properties (cf. EP-A 472 996). The activity of this substance is good; however at low application rates it is sometimes unsatisfactory.

Furthermore, it is already known that fenamidone can be employed for controlling fungi (cf. EP-A 0 629 616). However, the activity of fenamidone at low application rates is not always satisfactory.

It has now been found that the novel active compound combinations of valinamide derivatives of the general formula (I)

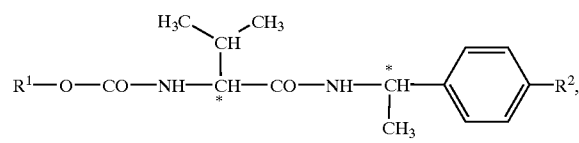
(I)

in which
R$^1$ represents i-propyl or s-butyl and
R$^2$ represents chlorine, methyl, ethyl or methoxy, and
fenamidone of the formula (II)

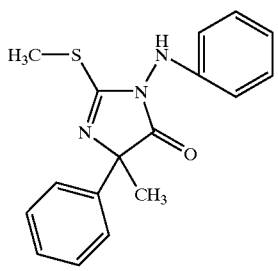
(II)

have very good fungicidal properties.

Surprisingly, the fungicidal activity of the active compound combinations according to the invention is considerably higher than the sum of the activities of the individual active compounds. This is an unforeseeable true synergistic effect and not just a complementation of action.

From the structural formula for the active compounds of the formula (I) it can be seen that the compounds have two asymmetrically substituted carbon atoms. The product can therefore be present as a mixture of various isomers or else in the form of an individual isomer.

Preferred compounds of the formula (I) are compounds in which the amino acid moiety is formed by i-propyloxycarbonyl-L-valine or sec-butyloxycarbonyl-L-valine and the phenethylamine moiety is either racemic or has the S-(−)-configuration, but in particular the R-(+)-configuration.

Particularly preferred compounds of the formula (I) are the compounds in which
R$^1$ represents i-propyl.

In particular, the compounds
1-methylethyl [2-methyl-1-[[[-1-(4-chlorophenyl)ethyl]amino]carbonyl]-propyl]-carbamate of the formula (Ia)

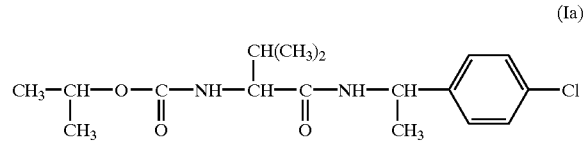
(Ia)

1-methylethyl [2-methyl-1-[[[-1-(4-methylphenyl)ethyl]amino]carbonyl]-propyl]-carbamate of the formula (Ib)

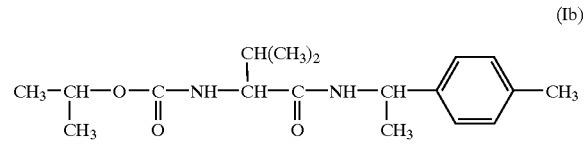
(Ib)

1-methylethyl [2-methyl-1-[[[-1-(4-ethylphenyl)ethyl]amino]carbonyl]-propyl]-carbamate of the formula (Ic)

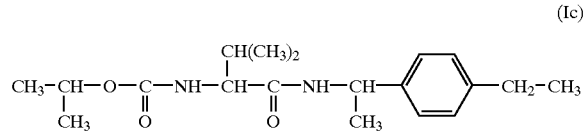
(Ic)

and 1-methylethyl [2-methyl-1-[[[-1-(4-methoxyphenyl)ethyl]amino]carbonyl]-propyl]-carbamate of the formula (Id)

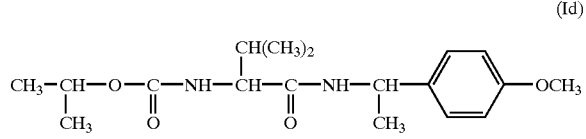
(Id)

and their isomers, as mentioned above, may be mentioned.

The active compounds of the formula (I) are known (cf. EP-A-0 472 996).

The fungicidally active compound fenamidone, which is furthermore present in the combinations according to the invention, is also known (cf. EP-A 0 629 616).

In addition to at least one active compound of the formula (I), the active compound combinations according to the invention comprise the active compound fenamidone of the formula (II). They may additionally also comprise other fungicidally active admixture components.

If the active compounds in the active compound combinations according to the invention are present in certain ratios by weight, the synergistic effect is particularly pronounced. However, the ratios by weight of the active compounds in the active compound combinations can be varied within a relatively wide range. In general,
from 0.1 to 10 parts by weight, preferably
from 0.2 to 2 parts by weight of active compound of the formula (II)
are present per part by weight of active compound of the formula (I).

The active compound combinations according to the invention have very good fungicidal properties and can be employed in particular for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for the protective control of Phytophthora infestans and Alternaria spec. on tomatoes and potatoes, and of Plasopara viticola on grapevines.

The fact that the active compound combinations are well tolerated by plants at the concentrations required for controlling plant diseases permits the treatment of above-ground parts of plants, of propagation stock and seeds, and of the soil.

The active compound combinations according to the invention can be converted into the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

In the formulations, the active compound combinations according to the invention can be present as a mixture with other active compounds such as fungicides, insecticides, acaricides and herbicides, and as mixtures with fertilizers or plant growth regulators.

Mixing partners for such mixtures are, for example:
Fungicides
2-aminobutane; 2-anilino-4-methyl-6-cyclopropyl-pyrimidine; 2',6'-dibromo-2-methyl-4'-trifluoromethoxy-4'-trifluoro-methyl- 1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, funnecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozcb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforin, triticonazole, validamycin A, vinclozolin, zineb, ziram.
Bactericides
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, AC 303 630, acephate, acrinathrin, alanycarb, aldicarb, alphamethrin, amitraz, avernectin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chloretoxyfos, chlorfenvinphos, chlorfluazuron, chlomiephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethlrin, demneton M, demeton S, demeton-S-methyl, diafenthiuron, diazinon, dichlofenthion, diclilorvos, dicliphos, -dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythirinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothlrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum;, pyridaben, pyrimidifen, pyriproxifen, quinalphos, RH 5992, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

In the treatment of parts of plants, the active compound concentrations in the use forms can be varied within a relatively wide range. In general, they are between 1 and 0.0001% by weight, preferably between 0.5 and 0.001%.

In the treatment of the seeds, amounts of active compound of generally from 0.001 to 50 g per kilogram of seed, preferably from 0.01 to 10 g, are required.

In the treatment of the soil, active compound concentrations of from 0.00001 to 0.1% by weight, preferably from 0.0001 to 0.02% by weight, are required at the site of action.

The good fungicidal activity of the active compound combinations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S.R., "Calculating Synergistic and Antagonistic Responses of Herbicide Combinations", Weeds 15, pages 20–22, 1967):

X is the efficacy, expressed in % of the untreated control, when applying the active compound A at a concentration of m g/ha, Y is the efficacy, expressed in % of the untreated control, when applying the active compound B at a concentration of n g/ha, E is the expected efficacy, expressed in % of the untreated control, when applying the active compound A and B at a concentration of m and n g/ha, $$\text{then} \quad E = X + Y - \frac{X \cdot N}{100}.$$

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

EXAMPLE

Plasmopara Test (Grapevine)/Protective

To produce a suitable preparation of active compound, either commercial active compound formulations (individual active compounds or active compound combinations) or 1 part by weight of active compound are mixed with 4.7 parts by weight of solvent (acetone) and 0.3 parts by weight of emulsifier (alkyl-aryl polyglycol ether), and the mixture is diluted with water to the particular desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at approximately 20° C. and 100% relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

The observed activity of the active compound combination according to the invention is greater than the calculated activity, i.e. a synergistic effect is present. At a mixing ratio of 1:1 and an application rate of 5 g/ha, the combination iprovalicarb and fenamidone has an actual efficacy of 98%. The expected value calculated using Colby's formula is, at 45%, considerably lower.

What is claimed is:

1. An active compound combination, comprising a synergistic fungicidally effective combination of:
   a) a first active compound comprising at least one valinamide derivative of the Formula (I)

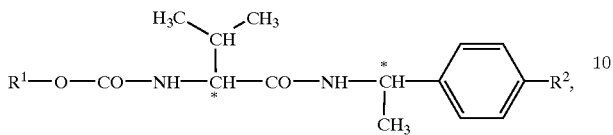

(I)

in which
R$^1$ represents i-propyl or s-butyl and
R$^2$ represents chlorine, methyl, ethyl or methoxy; and
a second active compound comprising a fenamidone of Formula (II)

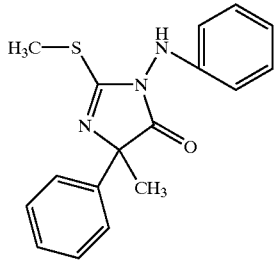

(II)

wherein the weight ratio of said first active compound of the Formula (I) to said second active compound of the Formula (II) is from 1:0.1 to 1:10.

2. A fungicidal composition comprising an active compound combination as defined in claim 1 and one or more agents selected from the group consisting of extenders and surfactants, wherein the weight ratio of said active compound of the Formula (I) to said active compound of the Formula (II) in said fungicidal composition is from 1:0.1 to 1:10.

3. An active compound combination, comprising a synergistic fungicidally effective combination of:
   a) a first active compound comprising at least one valinamide derivative of the Formula (I)

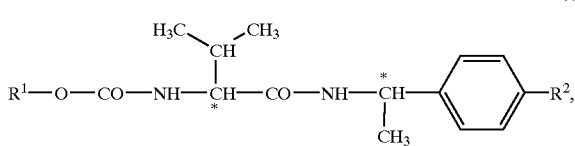

(I)

in which
R$^1$ represents i-propyl or s-butyl and
R$^2$ represents chlorine, methyl, ethyl or methoxy; and
a second active compound comprising a fenamidone of Formula (II)

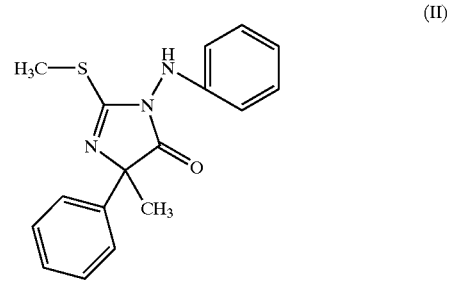

(II)

4. An active compound combination according to claim 1 wherein the weight ratio of said first active compound of the Formula (I) to said second active compound of the Formula (II) is from 1:0.2 to 1:2.

5. A method for controlling fungi, comprising the step of applying a fungicidally effective amount of an active compound combination as defined in claim 1 to a member selected from the group consisting of said fungi, a habitat of said fungi and combinations thereof.

6. A process for preparing a fungicidal composition, comprising the step of mixing an active compound combination according to claim 1 with one or more agents selected from the group consisting of extenders and surfactants.

* * * * *